United States Patent [19]

Costello et al.

[11] 4,236,018

[45] Nov. 25, 1980

[54] PROCESS FOR PREPARING CYCLOPROPANE CARBOXYLIC ACIDS

[75] Inventors: Alan T. Costello; Robert J. Lindsay, both of Manchester, England

[73] Assignee: Imperial Chemical Industries Limited, London, England

[21] Appl. No.: 56,305

[22] Filed: Jul. 10, 1979

[30] Foreign Application Priority Data

Jul. 18, 1978 [GB] United Kingdom ............... 30216/78

[51] Int. Cl.³ ..................... C07C 69/747; C07C 61/16
[52] U.S. Cl. ..................................... 560/124; 562/506
[58] Field of Search ................. 560/124; 562/401, 506

[56] References Cited

U.S. PATENT DOCUMENTS

| 2,433,500 | 12/1947 | Wood | 562/506 X |
| 2,466,679 | 4/1949 | Bruson et al. | 562/506 X |
| 2,815,362 | 12/1957 | Harper | 562/506 X |
| 3,277,171 | 10/1966 | Hopkins | 562/506 X |
| 3,567,749 | 3/1971 | Neugebauer et al. | 560/124 X |

OTHER PUBLICATIONS

C.F.H. Allen et al., *Canadian Journal of Research* 9:159–168, (1933).

*Primary Examiner*—Natalie Trousof
*Assistant Examiner*—Vera C. Clarke
*Attorney, Agent, or Firm*—Cushman, Darby & Cushman

[57] ABSTRACT

1-Cyano-3-[2',2'-(dihalogeno and/or trifluoromethyl)-vinyl]-2,2-dimethylcyclopropanes are converted into the corresponding 1-amides and 1-carboxylic acids by reaction with sulphuric acid and water, or into the corresponding 1-carboxylic acid esters by reaction with sulphuric acid, water and a lower alkanol. High yields are obtained.

5 Claims, No Drawings

PROCESS FOR PREPARING CYCLOPROPANE CARBOXYLIC ACIDS

This invention relates to a chemical process and more particularly to a process for the preparation of certain cyclopropane carboxylic acids and derivatives thereof.

Esters, such as the m-phenoxybenzyl ester, of 3-(2',2'-dichlorovinyl)-2,2-dimethylcyclopropane-1-carboxylic acid (I).

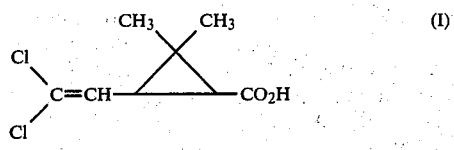

are valuable insecticides.

Our cognate copending United Kingdom Application Nos. 48078/76 and 22046/77 describe and claim a process for the preparation of a compound of the formula:

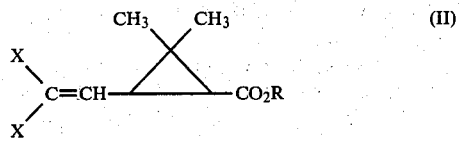

wherein R represents a hydrogen atom or a lower alkyl group and X represents a chlorine or a bromine atom, which comprises (a) the step of alkaline hydrolysis of a cyclopropane carboxylic acid ester of the formula:

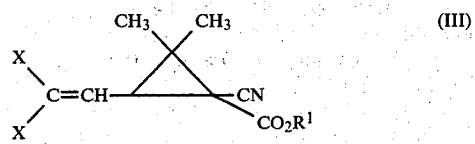

wherein $R^1$ has the same meaning as R above and may be the same or different, and X has the meaning defined above, (b) the step of decarboxylation of the compound of formula:

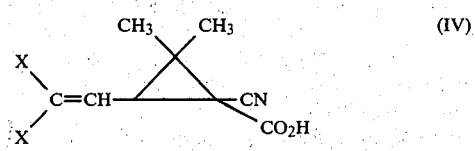

obtained in step (a) by heating the compound in a polar aprotic solvent, (c) the step of treating the compound of the formula:

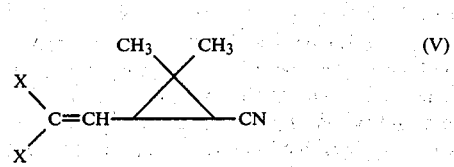

obtained in step (b) with dry hydrogen chloride in an alcohol R.OH wherein R has the meaning defined above, the reaction occurring with concurrent alcoholysis or being followed by a hydrolysis step whereby a carboxylic acid ester or carboxylic acid of formula (II) above is obtained.

Compounds of formula (V) exist in cis and trans isomeric forms, according to whether the -CN and -CH=$CX_2$ groups are on the same side or opposite sides respectively of the cyclopropane ring, and the same is true of the derived compounds of formula (II) with respect to the -$CO_2$R and -CH=$CX_2$ groups and of the intermediate stage compounds (III) and (IV).

The process described above enables the cis-and trans isomers of the compounds of formula (II) to be prepared separately, because at step (c) of the process the trans-isomer of the compound of formula (V) can be reacted preferentially, leaving the cis-isomer unchanged. The latter can then be separated and subjected separately to the reaction of step (c). This is a valuable feature of the process, because the cis-isomers of insecticidal esters of formula (I) have greater insecticidal potency than the corresponding trans-isomers. Consequently, the highly active cis-isomers of (I) can be obtained essentially free from the less active transisomers.

The present invention provides an alternative route to certain cyclopropanecarboxylic acids and derivatives thereof from the corresponding nitriles.

According to the present invention there is provided a process for the preparation of a compound of the general formula:

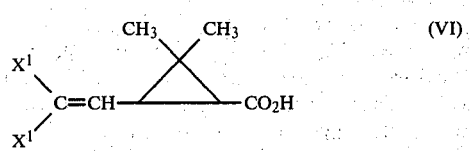

or a compound of the general formula:

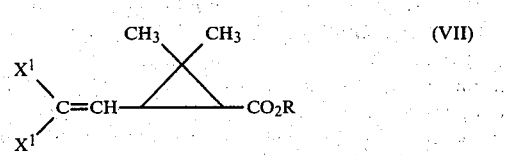

wherein each $X^1$ represents a chlorine or bromine atom or a -$CF_3$ group, or one $X^1$ represents a chlorine or bromine atom and the other represents a -$CF_3$ group, and R represents a lower alkyl group, which comprises the steps of:

(i) reacting a compound of the general formula:

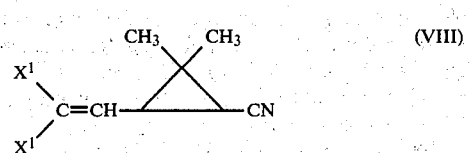

wherein $X^1$ has the meaning stated above, with sulphuric acid and water to give a compound of formula:

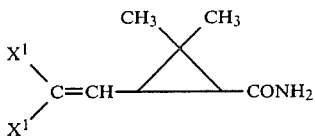

(IX)

and (ii) either (a) further reacting the compound of formula (IX) with sulphuric acid and water to give a compound of formula:

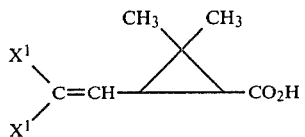

(VI)

or (b) reacting the compound of formula (IX) with sulphuric acid, water and an alcohol of the formula R.OH, in which R has the meaning stated above, to give a compound of formula:

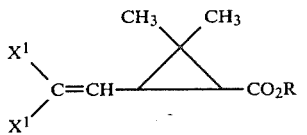

(VII)

The individual steps (i) and (ii) of the above process are also features of the invention.

The reaction conditions for obtaining optimum yields in the first step of the above process, i.e. hydrolysis of the nitrile (VIII) to the carboxylic acid amide (IX), are somewhat critical.

The ordinary "concentrated" sulphuric acid of commerce, which contains approximately 98% by weight of sulphuric acid and approximately 2% by weight of water, can be used in the process without additional water. The yield of amide (IX) which is obtained is dependent on the amount of sulphuric acid relative to the amount of nitrile (VIII), and on the reaction time and temperature. In general, using 98% sulphuric acid the reaction temperature should not exceed 50° C. and is preferably approximately 30° C., and the amount of sulphuric acid should be sufficient to provide at least 1 mol of water per mol of nitrile (VIII). Theoretically, approximately 9 moles of 98% sulphuric acid contain 1 mol of water, but in practice less than this amount of acid per mol of nitrile can be used because concentrated sulphuric acid very quickly absorbs moisture from the atmosphere unless strict precautions are taken to prevent it. Reaction times from approximately 2 to approximately 24 hours may be used.

It is preferred to use water in the reaction additional to that which is contained in "concentrated" sulphuric acid, and up to 30 mols of water per mol of nitrile (VIII) may be used, although excessive dilution of the sulphuric acid is to be avoided because the rate of reaction is adversely affected and the reaction may not go to completion. In general, the use of additional water permits higher reaction temperatures, for example, up to 100° C., to be used.

Preferred conditions for the conversion of nitrile (VIII) into amide (IX) are 4 mols of sulphuric acid and 6 moles of water per mol of nitrile at a temperature of 80° C. for 6 hours. The yield of amide under these conditions is almost quantitative. The amide may be obtained from the reaction mixture by cooling the latter, drowning it into water and extracting the amide from the liquor with a water-immiscible organic solvent, for example, toluene. The amide may then be isolated by removing the organic solvent by conventional means, for example, by evaporation or by distillation, optionally under reduced pressure.

In carrying out step (ii)(a) of the process, i.e. conversion of the amide of formula (IX) obtained in step (i) into the carboxylic acid of formula (VI), it is not necessary to isolate the amide. Conveniently, more water is added to the reaction mixture at the conclusion of step (i) and the diluted mixture is then heated in order to hydrolyse the amide (X) to the acid (VI). Typically, the reaction mixture may be heated at 100° C. for 12 hours but considerable variations in reaction conditions are possible without adverse effect on the yield and quality of the product. An amount of 4 to 5 mols of water per mol of sulphuric acid is suitable for carrying out this stage of the process. If desired, the amide (IX) from step (i) may be isolated as described above and then hydrolysed using a suitable strength of sulphuric acid to give the carboxylic acid (VI). Yields of carboxylic acid of formula (VI) of 90% or even higher are readily attainable using the process described above.

The carboxylic acid may be isolated from the reaction mixture by drowning the latter into water, extracting the aqueous liquors with a water-immiscible organic solvent, for example, toluene, extracting the toluene extract with a dilute aqueous solution of an alkali, for example, sodium hydroxide, followed by acidification of the aqueous alkaline extract to precipitate the carboxylic acid.

Step (ii)(b) of the process, i.e. conversion of the amide of formula (IX) obtained in step (i) into the carboxylic acid ester (VII) is effected by heating the amide in a mixture of sulphuric acid, water and alcohol of formula R.OH. The presence of water at this stage is essential, otherwise low yields (i.e. 10%) are obtained. The reaction may be carried out without isolation of the amide by adding the alcohol R.OH to the reaction mixture obtained at the conclusion of step (i), and then heating the resulting mixture containing the amide, sulphuric acid, water and alcohol in order to convert the amide (IX) into the carboxylic acid ester (VII). Reaction conditions for preparation of the ester are similar to those in step (ii) (a) for preparation of the carboxylic acid, a reaction temperature of 100° C. for 12 hours being suitable. Amounts of 1 to 2 mols of each of water and the alcohol R.OH per mol of sulphuric acid are suitable for carrying out this stage of the process.

If desired, the amide of formula (IX) may be isolated before being converted into the carboxylic acid ester of formula (VII) by reaction with sulphuric acid, water and alcohol R.OH as described above.

Yet again, the nitrile of formula (VIII) may be converted directly into the carboxylic acid ester of formula (VII) by reaction with sulphuric acid, water and alcohol R.OH without intermediate preparation of the amide of formula (IX), and this constitutes a further feature of the invention. This single-stage process may be carried out, for example, by mixing together the sulphuric acid and water, adding to the cooled mixture a mixture of the nitrile of formula (VIII) and the alcohol R.OH, and heating the four-component mixture so obtained to effect alcoholysis of the nitrile to give the carboxylic acid ester. Conveniently, reaction may be carried out at the reflux temperature of the mixture, a reaction time of approximately 12 hours being generally suitable.

The carboxylic acid ester prepared by any of the methods described above may be isolated by drowning the reaction mixture, preferably after cooling, into water, extracting the aqueous mixture with a water-immiscible organic solvent, for example, toluene, and recovering the ester from the extract by removal of the organic solvent by evaporation or distillation, optionally under reduced pressure.

Hitherto, the stability of the cyclopropane ring towards strong acids has been in doubt. Thus, C. F. H. Allen and R. Boyer (Canadian Journal of Research, Volume 9, pages 159–168 (1933)) found that ethyl 1-1-cyanocyclopropane-1-carboxylate with 14 mols per mol of sulphuric acid at room temperature overnight gave the corresponding ester amide, but the yield was low (35%). Surprisingly, it has been found that provided the reaction conditions described above are adhered to, cyclopropane nitriles of formula (VIII) can be converted in the presence of sulphuric acid into the corresponding amide (IX) and also into the corresponding carboxylic acid (VI) and carboxylic acid ester (VII) in very good yields, and without adverse effect on the cis-trans isomer ratio of the products.

The invention is illustrated but not limited by the following Examples in which parts and percentages are by weight.

EXAMPLE 1

Preparation of 3-(2',2'-dichlorovinyl)-2,2-dimethylcyclopropane-1-carboxylic acid amide 5.5 Parts of water are added carefully below 30° C. to 19.5 parts of concentrated (98% w/w) sulphuric acid. The solution is cooled below 20° C. and 16.5 parts of 1-cyano-3-(2',2'-dichlorovinyl)-2,2-dimethylcyclopropane (57.4% strength; cis/trans isomer ratio 67:33) are added dropwise, the temperature being maintained below 20° C. by external cooling. The reaction mixture is then stirred at 80° C. for 6 hours, cooled to 20° C., drowned into 100 parts of water and extracted with toluene (2×50 parts). The toluene extracts are combined and the toluene is evaporated off under reduced pressure to give 15.8 parts of 3-(2',2'-dichlorovinyl)-2,2-dimethylcyclopropane-1-carboxylic acid amide containing 42.8% of the cis-isomer and 20.2% of the trans-isomer. The yield is 96%.

EXAMPLE 2

Preparation of 3-(2',2'-dichlorovinyl)-2,2-dimethylcyclopropane-1-carboxylic acid 5.5 Parts of water are added carefully below 30° C. to 19.5 parts of concentrated (98% w/w) sulphuric acid. The solution is cooled below 20° C. and 16.5 parts of 1-cyano-3-(2',2'-dichlorovinyl)-2,2-dimethylcyclopropane (57.4% strength, cis/trans isomer ratio 67:33) are added dropwise, the temperature being maintained below 20° C. by external cooling. The reaction mixture is then stirred at 80° C. for 6 hours and then cooled below 30° C. 10 Parts of water are added below 50° C. The mixture is then heated at 100° C. for a further 12 hours, cooled to 20° C. and drowned into 100 parts of water. The aqueous mixture is extracted with toluene (2×50 parts), the toluene extracts are combined and then extracted with 5% aqueous sodium hydroxide solution (2×50 parts). The aqueous alkaline extracts are separated, combined and acidified with dilute sulphuric acid to precipitate the product which is filtered off and dried. 9.6 Parts of 3-(2',2'-dichlorovinyl)-2,2-dimethylcyclopropane-1-carboxylic acid containing 55.6% of the cis-isomer and 32.6% of the trans-isomer are obtained. The overall yield is 90%.

EXAMPLE 3

Preparation of Ethyl 3-(2',2'-dichlorovinyl)-2,2-dimethylcyclopropane-1-carboxylate The procedure described in Example 2 is repeated up to the point at which the mixture of 1-cyano-3-(2',2'-dichlorovinyl)-2,2-dimethylcyclopropane, sulphuric acid and water has been heated and stirred at 80° C. for 6 hours and then cooled below 30° C. 16 Parts of ethanol are added to the reaction mixture below 50° C. The mixture is then heated at 100° C. for a further 12 hours, cooled to 20° C. and drowned into 100 parts of water. The aqueous mixture is extracted with toluene (2×50 parts), the toluene extracts are combined and the solvent is removed by evaporation under reduced pressure. There are obtained 17.6 parts of ethyl 3-(2',2'-dichlorovinyl)-2,2-dimethylcyclopropane-1-carboxylate as a brown oil containing 40.4% of the cis-isomer and 21.8% of the trans-isomer. The overall yield is 92.4%.

EXAMPLE 4

Preparation of Ethyl 3-(2',2'-dichlorovinyl)-2,2-dimethylcyclopropane-1-carboxylate from the nitrile without intermediate preparation of the amide 16.6 Parts of concentrated (98% w/w) sulphuric acid are stirred and 5 parts of water are added, the mixture being maintained below 20° C. by external cooling. 8.25 parts of 1-cyano-3-(2',2'-dichlorovinyl)-2,2-dimethylcyclopropane (57.4% strength; cis/trans isomer ratio 67:33) are dissolved in 25 parts of ethanol and the solution is added to the sulphuric acid/water mixture keeping the temperature below 30° C. The resulting mixture is then stirred and heated at the reflux temperature for 12 hours, cooled to 20° C. and drowned into 100 parts of water. The aqueous mixture is extracted with toluene (2×25 parts), the toluene extracts are combined and the solvent is removed by evaporation under reduced pressure. There are obtained 9.3 parts of ethyl 3-(2',2'-dichlorovinyl)-2,2-dimethylcyclopropane-1-carboxylate as a brown oil containing 36.3% of the cis-isomer and 22.2% of the trans-isomer. The yield is 92%.

We claim:

1. A process for the preparation of a cyclopropane carboxylic acid of the general formula:

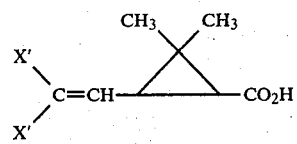

or a cyclopropane carboxylic acid ester of the general formula:

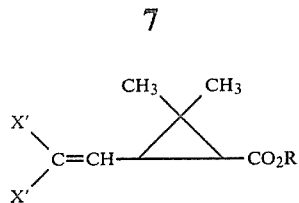

wherein each X' represents a chlorine or bromine atom or a -CF$_3$ group, or one X' represents a chlorine or bromine atom and the other represents a -CF$_3$ group, and R represents a lower alkyl group, which comprises the steps of:

(i) reacting a cyclopropane nitrile of the general formula:

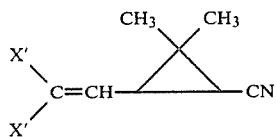

wherein X' has the meaning stated above, with either (A) a sulphuric acid and water solution containing 98% sulphuric acid in an amount to provide at least 1 mole of water per mole of cyclopropane nitrile, at a reaction temperature not exceeding 50° C. or (B) 4 moles of sulphuric acid and 6 moles of water per mole of cyclopropane nitrile at a reaction temperature of 80° C. for a reaction time of 6 hours to give an amide of the formula:

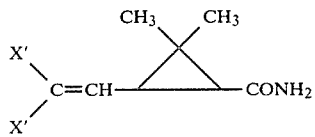

and (ii) either (a) diluting the cyclopropane amide-containing reaction mixture from step (i) with water to provide 4 to 5 mols of water per mole of sulphuric acid and heating the mixture to give a cyclopropane carboxylic acid of formula:

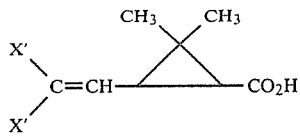

or (b) diluting the cyclopropane amide-containing reaction mixture from with at least an alcohol R.OH, wherein R has the meaning stated above, to get 1 to 2 moles each of water and the alcohol R.OH per mole of sulphuric acid followed by heating of the mixture to give a cyclopropane carboxylic acid ester of formula:

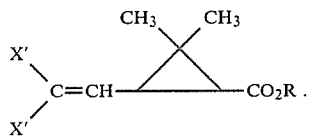

2. A process comprising step (i) of claim 1.
3. A process comprising step (ii) of claim 1.
4. A process for the preparation of a cyclopropane carboxylic acid ester having the formula defined in claim 1, which comprises reacting a cyclopropane nitrile having the formula defined in claim 1 with sulphuric acid, water and an alcohol R.OH.
5. A process as claimed in claim 4 wherein the sulphuric acid and water are mixed together, adding to the cooled mixture a mixture of the cyclopropane nitrile and the alcohol R.OH and heating the four-component mixture so obtained to effect alcoholysis of the nitrile to give the carboxylic acid ester.

* * * * *